(12) United States Patent
Siler-Khodr et al.

(10) Patent No.: US 7,834,141 B1
(45) Date of Patent: *Nov. 16, 2010

(54) NON-MAMMALIAN GNRH ANALOGS AND USES THEREOF IN TUMOR CELL GROWTH REGULATION AND CANCER THERAPY

(76) Inventors: Theresa Siler-Khodr, 13 Mayborough La., San Antonio, TX (US) 78257; Gabriel S. Khodr, 13 Mayborough La., San Antonio, TX (US) 78257

( * ) Notice: Subject to any disclaimer, the term of this patent is extended or adjusted under 35 U.S.C. 154(b) by 697 days.

This patent is subject to a terminal disclaimer.

(21) Appl. No.: 09/540,685

(22) Filed: Mar. 31, 2000

(51) Int. Cl.
*C07K 7/00* (2006.01)
*C07K 7/23* (2006.01)
*C07K 14/575* (2006.01)

(52) U.S. Cl. ............ 530/313; 530/328; 530/332; 530/333; 530/335; 514/2; 514/15

(58) Field of Classification Search ............ 530/356, 530/399; 514/2; 536/23.1; 435/69.1, 69.4
See application file for complete search history.

(56) References Cited

U.S. PATENT DOCUMENTS 6,323,179 B1 * 11/2001 Siler-Khodr ............... 514/15
6,635,739 B2 * 10/2003 Siler-Khodr ............... 530/300

FOREIGN PATENT DOCUMENTS

GB 2 237 571 A * 5/1991

OTHER PUBLICATIONS

Teplan, I. Role, mechanisim of action and application of gonadoliberins in reproductive processes. Acta Bioligica Hungarica 40 (1-2) 3-36 (1989).*
White et al. A second gene for gonadotropin-releasing hormone:cDNA and expresssion pattern in the brain. Proc. Natl. Acad. Sci. USA vol. 91 1423-1427 (1994).*
Lovejoy et al. Structural modifications of non-mammalian gonadotropin-releasing hormone (GnRH) isoforms: design of novel GnRH analogues. Regulatory Peptides vol. 60:99-115 (1995).*

* cited by examiner

*Primary Examiner*—Marianne P Allen
*Assistant Examiner*—Regina M DeBerry
(74) *Attorney, Agent, or Firm*—Gunn, Lee & Cave, P.C.; Robert L. McRae

(57) ABSTRACT

Specially designed non-mammalian GnRH analogs resistant to degradation by the tumor tissue enzymes, post-proline peptidases as well as endopeptidases, are disclosed. The GnRH analogs are further defined as analogs of chicken II GnRH, salmon GnRH, or herring GnRH, but can include any non-mammalian GnRH analog with similar amino acid structure. These non-mammalian analogs incorporate D-arginine, D-leucine, D-tBu-Serine or D-Trp or other similar amino acids at position 6 and ethylamide or aza-Gly-amide or similar amides at position 10. These analogs demonstrate preferential binding to tumor cell GnRH receptors that is greater relative to the binding of the mammalian analogs to the tumor cell GnRH receptor. These non-mammalian GnRH analogs may be used in pharmaceutical preparations, and it specifically in various treatments as an anti-tumor, anti-proliferation, anti-metastatic and/or an apoptotic agent. The non-mammalian GnRH analogs are also provided in pharmaceutical preparations that may be used clinically for tumor regression when used in very low doses and administered in pulsatile fashion.

7 Claims, 5 Drawing Sheets

| Analog of GnRH | |
|---|---|
| Mammalian | 30 |
| Lamprey | 20 |
| Salmon | 300 |
| Chicken I | 80 |
| Chicken II | 200 |
| Chicken II EA (10) | 130 |
| Chicken II D-Arg (6), aza-Gly (10) amide (SEQ ID NO. 2) | >200 |
| Salmon II D-Arg (6), aza-Gly (10) amide (SEQ ID NO. 4) | 200 |
| Mammalian D-Trp (6) | 20 |
| Mammalian EA (10) | 70 |
| Mammalian D-Trp (6), EA (10) | 60 |
| Mammalian D-Leu (6), EA (10) | 80 |
| Mammalian But-D-Ser (6), EA (10) | 110 |
| Mammalian Im-bzl-D-His (6), EA (10) | >200 |
| Antide | 120 |

FIG. 5

SEQUENCE LISTING

```
<160> NUMBER OF SEQ ID NOS: 7

<210> SEQ ID NO 1
<211> LENGTH: 30
<212> TYPE: DNA
<213> ORGANISM: Gallus gallus

<400> SEQUENCE: 1
cagcactggt ctcatggctg gtatcctgga                                     30

<210> SEQ ID NO 2
<211> LENGTH: 10
<212> TYPE: PRT
<213> ORGANISM: Gallus gallus
<220> FEATURE:
<221> NAME/KEY: mat_peptide
<222> LOCATION: (6)..(6)
<223> OTHER INFORMATION: Within brain mRNA 121-150, within brain gene
      2174-2203.  MOD_RES substitution of Gly residue at 10 by
      aza-Gly-NH2, ethylamide or other Gly amide.  Xaa represents D-Arg.
      MOD_RES Glu at position 1 is pyroglutamic acid.

<400> SEQUENCE: 2

Glu His Trp Ser His Xaa Trp Tyr Pro Gly
1               5                   10
```

-continued

```
<210> SEQ ID NO 3
<211> LENGTH: 30
<212> TYPE: DNA
<213> ORGANISM: Salmo salar

<400> SEQUENCE: 3
cagcactggt cttatggctg gctgcctgga                                          30

<210> SEQ ID NO 4
<211> LENGTH: 10
<212> TYPE: PRT
<213> ORGANISM: Salmo salar
<220> FEATURE:
<221> NAME/KEY: mat_peptide
<222> LOCATION: (6)..(6)
<223> OTHER INFORMATION: MOD_RES substitution of Gly residue at 10 with
      aza-Gly-NH2, ethylamide or other Gly amide.  Xaa represents D-Arg.
      MOD_RES Glu at position 1 is pyroglutamic acid.

<400> SEQUENCE: 4

Glu His Trp Ser Tyr Xaa Trp Leu Pro Gly
 1               5                  10

<210> SEQ ID NO 5
<211> LENGTH: 30
<212> TYPE: DNA
<213> ORGANISM: Clupea harengus

<400> SEQUENCE: 5
cagcactggt cttatggctg gctgcctgga                                          30

<210> SEQ ID NO 6
<211> LENGTH: 10
<212> TYPE: PRT
<213> ORGANISM: Clupea harengus
<220> FEATURE:
<221> NAME/KEY: mat_peptide
<222> LOCATION: (6)..(6)
<223> OTHER INFORMATION: MOD_RES substitution of Gly residue at 10 with
      aza-Gly-NH2, ethylamide or other Gly amide.  Xaa represents D-Arg.
      MOD_RES Glu at position 1 is pyroglutamic acid.

<400> SEQUENCE: 6

Glu His Trp Ser Tyr Xaa Leu Ser Pro Gly
 1               5                  10

<210> SEQ ID NO 7
<211> LENGTH: 10
<212> TYPE: PRT
<213> ORGANISM: Gallus gallus
<220> FEATURE:
<221> NAME/KEY: mat_peptide
<222> LOCATION: (6)..(6) and (10)..(10).
<223> OTHER INFORMATION: Within brain mRNA 121-150, within brain gene
      2174-2203.  MOD_RES Glu at position 1 is pyroglutamic acid.  Xaa
      at position 6 represents any D-amino acid.  Xaa at posiiton 10
      represents aza-Gly-NH2, ethylamide or other similar amide.

<400> SEQUENCE: 7

Glu His Trp Ser His Xaa Trp Tyr Pro Xaa
 1               5                  10
```

NON-MAMMALIAN GNRH ANALOGS AND USES THEREOF IN TUMOR CELL GROWTH REGULATION AND CANCER THERAPY

BACKGROUND OF THE INVENTION

1. Field of the Invention

Applicants' invention relates to the field of tumor growth regulation. More particularly, Applicants' invention concerns unique non-mammalian peptide hormone analogs of non-mammalian gonadotropin releasing hormone (GnRH) and the method for use of these analogs in the regulation of cell growth, particularly cancer cell growth.

2. Background Information

Gonadotropin-releasing hormone (GnRH) is a hormone known to be produced in the hypothalamus with binding affinity for the pituitary gland. When hypothalamic GnRH binds to the pituitary it causes the pituitary gland to release the gonadotropins (i.e. gonad stimulating hormones) luteinizing hormone (LH) and follicle-stimulating hormone (FSH). Each of these pituitary hormones has a different effect depending on one's sex. One important effect is the production and secretion of the gonadal steroids estrogen and progestogen in sexually mature females and testosterone in males.

Before the chemical characterization of the mammalian GnRH it was realized that a hypothalamic substance regulated the production of pituitary LH and FSH (1) and that these gonadotropins regulated gonadal steroidogenesis. The delineation of mammalian GnRH enabled Applicants to synthesize this decapeptide and administer it systemically to humans (2). It was then recognized that a long acting superagonist of this mammalian GnRH effected a flare release of pituitary gonadotropins followed by their inhibition (3). The inhibition was effected by a down-regulation of the pituitary GnRH receptor which corresponded testosterone. This is a form of chemical castration.

Since certain types of tumors, such as certain breast (4) and prostate cancers (5), are now known to be dependent on gonadal steroids, mammalian GnRH analogs have been used to suppress gonadal steroids via their chemical castration activity (3). Thus, we know that the use of mammalian GnRH analogs is feasible as a treatment of certain cancers.

It was only with the development of sensitive and specific radioimmunoassays for GnRH and GnRH-like molecules that a very surprising finding was reported. That finding was initially described by Applicants. Applicants reported that GnRH-like molecules exist and function not only in the hypothalamic-pituitary axis, which functions as an endocrine system to distribute hormone systemically, but GnRH-like molecules also exist in extra-hypothalamic tissues (6-9) to provide a paracrine action i.e. localized signal secretion. It is now realized that paracrine action of GnRH-like substances have functions in the placenta, gonad, breast, prostate, etc., (10-13) as well as in many cancerous tumors (14-31). Even with this general knowledge, the effective use of mammalian GnRH analogs to act directly on particularly tumor tissue has not resulted. One of the goals of the present invention was to utilize novel forms of GnRH not previously envisioned for cancer therapy that bind to the tumor GnRH-like receptor with 50 to 1000 fold the activity of mammalian GnRH or its superagonist and have potent bioactivity in inhibiting tumor cell growth.

The initial studies on GnRH activity in tumor tissues and the human placenta utilized mammalian GnRH and its analogs, in accordance with the teaching that the human encodes for only one isoform of GnRH (32,33). In Applicants' studies in the human placenta Applicants localized and quantified the concentration of GnRH produced by the human placenta throughout pregnancy (34,35). Applicants demonstrated the synthesis and activity of a GnRH-like molecule in regulating human chorionic gonadotropin (hCG) and steroid production (36-38), and the release of a GnRH-like molecule into the maternal circulation (34). Applicants also demonstrated that high doses of mammalian GnRH could stimulate hCG and prostanoid production in a specific receptor mediated event and that GnRH-like production and activity in the human placenta is regulated by feedback interactions of estrogens and progesterone production (39-41). Thus, Applicants described and established the first paracrine system in human or mammalian physiology (42-45). Concomitantly, Dubois et al. (12) described a second paracrine system from the presence of somatostatin in the pancreas. Thereafter, Applicants and other investigators reported actions of mammalian GnRH on placental function and identified feedback interactions including activin, inhibitin, follistatin, neurotransmitters, prostaglandins, and steroids (46-63).

Using in situ localization a message to mammalian GnRH has been localized at the syncytio- and cytotrophoblast, as well as the stroma of the placenta (64-66). A gene for mammalian GnRH differing from hypothalamic GnRH by the inclusion of the first intron and a very long first exon has been reported (67-69). Multiple transcription sites have been identified for the GnRH gene in the placenta as well as in other reproductive tissues (70-72). Steroid regulatory sites on the promoter have also been identified (73,74). The functionality of the promoter is supported by the demonstration that mRNA for GnRH can be regulated by steroids (75-78).

Placental GnRH receptor activity and a GnRH mRNA have also been identified (79,80). The receptor number is highest in early gestation and down-regulated by 12-20 weeks, and still detectable in term placenta, although the mRNA for mammalian GnRH is not (79,80). This pattern of receptor activity parallels that of chorionic GnRH-like activity (6,34) and supports the hypothesis that chorionic GnRH may down-regulate its receptor, as does mammalian GnRH and its analogs at the pituitary level. Studies of Szilagyi et al. (81) and Currie et al. (82) have indicated down-regulation of chorionic receptors by mammalian GnRH analogs. In addition, estradiol has been shown to upregulate the placental GnRH receptor. Thus, there is substantial data to indicate a functional, regulated GnRH receptor in extrahypothalamic tissues.

In total, these studies have firmly established the presence of a hypothalamic-pituitary-gonadal axis in extra-hypothalamic tissue. Presently many other hypothalamic-like activities, such as by corticotropin-releasing hormone (CRH), have now been defined in the placenta and other tissues as well. Such paracrine axis are known in the pancreas, thyroid, gut, bone, brain, ovary, endometrium, eye, etc.

Of particular interest to this invention are previous reports of the presence of GnRH-like substances and receptors in numerous cancer tissues and their cell lines (15,17,20,23,25, 26,30,31,83,84). GnRH-like activity and its receptors have been identified in the breast, bronchial, ovarian, endometrial, prostate, gastrointestinal tumors. The function of a GnRH-like substance and its receptors in tumor tissues is supported by the demonstration that mammalian GnRH can stimulate hCG from human and animal tumors and can inhibit cell growth in vitro. These findings have led to numerous studies of the effects of mammalian GnRH analogs on the expression of GnRH receptors, cell signal transduction, apoptosis, and overall growth of tumor cell lines (14,16,18,19,21,22,29,85-89). The growth of tumors in vivo has also been studied with individual case reports of patients responsive to mammalian GnRH analogs (24,27,28,90-92).

However, some very problematic findings from previous studies in both the placenta and tumor tissue has led to skepticism about the true role of mammalian GnRH analogs in both tissues. The GnRH receptor affinity for GnRH in both the placenta and tumors is on the order of $10^{-5}$ to $10^{-6}$ M (84,93,94). The biological significance of such a weak affinity in light of much lower levels of endogenous GnRH-like activity must be questioned. In addition, Applicants have observed in human pregnancy studies, both in vitro and in vivo, that mammalian GnRH appears to act as a partial agonist not a true agonist of tumor GnRH (38,95). When receptors are available, mammalian GnRH acts as an agonist of tumor GnRH, but when tumor receptors are low or occupied, mammalian GnRH competes with the more potent tumor GnRH resulting in a partial agonist action. Furthermore, Applicants and others have observed that certain antibodies for mammalian GnRH reacted with chorionic GnRH with a different affinity (96-99). These findings led Applicants to propose that neither the extra-hypothalamic GnRH nor its receptor are identical to mammalian GnRH and its pituitary receptor (100,101).

Applicants have defined yet another difference in extra-hypothalamic GnRH, i.e., its metabolism. The metabolism of a hormone is as important for maintaining biologically active concentrations of that hormone, as that which stimulates the hormone's synthesis and release. For GnRH, in the non-pregnant human, both in the pituitary and in the circulation, the predominant enzymatic degradation is directed to the 5-6 peptide bond catalyzed by an endopeptidase. Thus, existing analogs of the mammalian GnRH each bear a D-amino acid substituted in the 6 position. However, Applicants have isolated and characterized the dominant enzyme that degrades GnRH in the placenta and it is a post-proline peptidase acting to cleave the proline-glycine peptide bond at the 9-10 position (102,103). Applicants have recently obtained similar data for the metabolism of GnRH in breast tumor cells. Thus, there appears to be cell specific metabolism of GnRH at the placenta and breast tumor cells which differs from that in blood and the pituitary.

Since it appeared as though there was a different form of GnRH at work at the placenta and breast tumor cells, various isoforms of GnRH were investigated. Different isoforms of GnRH have been identified in non-mammalian species, such as fish and ayes. The unique sequence of these GnRH are known. Chicken I, chicken II, salmon, catfish, dogfish, lamprey and more recently herring GnRH have also been reported (33,106). In lower vertebrates a number of GnRH isoforms can be expressed in the same species (32,33,76,78, 105,107-116). In most cases, each decapeptide conserves the first four, the sixth and in every case, the last two amino acids in the GnRH molecule, but have varying amino acids in the fifth, seventh and/or eighth position. These modifications render the molecule unique, having only weak affinity for the mammalian pituitary receptor, although conversely mammalian GnRH is active in many lower vertebrate classes.

As mentioned, in certain lower vertebrates a number of GnRH isoforms are expressed in the same species. In amphibians, a chicken II GnRH receptor as well as a mammalian GnRH receptor has been reported. However, it was not until 1994, when Dellovade et al. (117) and King et al. (118) described chicken II GnRH in musk shew, mole and bat brain, that the existence of multiple isoforms of GnRH in a mammal was realized. Even then, it was still thought that modern placental mammalian species did not encode or express other than mammalian GnRH. Recently however, chicken II GnRH has been characterized in the tree shew (119), guinea pig, and primate brain (120) and their separate genes have been described (121,122). Only this year has the code for the chicken II GnRH receptor been identified in human tissues.

In contrast, Applicants have proposed and obtained substantial data to support the hypothesis that non-mammalian isoforms of GnRH and their specific receptors are expressed in extra-hypothalamic tissues and that the non-mammalian GnRH molecules are the true ligands for these receptors (123,124). Applicants have also proposed that these GnRH molecules have specific roles in regulating cell growth and cell death and are pivotal in regulating cell growth of GnRH responsive tumors by a direct receptor mediated action on these tumor cells.

It is believed that the non-mammalian GnRH isoforms and analogs of the present invention may act either as a superagonist at the tumor tissue leading to tissue receptor down-regulation, or as a pure antagonist of the endogenous isoform of GnRH in the tumor tissue, acting via the tumor tissue receptor. The down-regulation of the GnRH receptor or the antagonism of the endogenous isoform of GnRH will provide for a reduction in cell proliferation and/or induce apoptosis. The specific action of the non-mammalian GnRH analog will compete at the tumor cell GnRH receptor(s) with the endogenous isoform of GnRH effecting an antagonism or a super-agonistic down-regulation of the receptor, leading to cell death and regression of the tumor and inhibition of metastasis. Thus, this agent may be used to reduce tumor growth. To date, no such non-mammalian GnRH analog has been designed which has stability and tumor tissue specificity.

To date, little if any data, has been reported in relation to non-mammalian GnRH activity on tumor tissues. Chicken I GnRH and Lamprey GnRH (18,86,125,126) have been studied and limited activity was found. Applicants have studied these isoforms of GnRH and have found no or limited binding activity in chorionic tissues. On the other hand, Applicants have demonstrated greatly enhanced binding and bioactivity of chicken II GnRH and salmon GnRH analogs as compared to mammalian GnRH or its analogs in both breast cancer cells and placental tissue. Thus, Applicants have obtained data to support the hypothesis that certain non-mammalian GnRH analogs have enhanced receptor and bioactivity for tumor tissues and this finding taken together with the understanding of the unique metabolism of GnRH isoforms in cell specific sites have formed the basis of Applicants invention, i.e., the utilization of stable, cell-active analogs of non-mammalian GnRH isoforms to regulate tumor cell growth and the treatment of cancer. In addition, Applicants postulate that due to similar amino acid structures, Herring GnRH, Dogfish GnRH, and Catfish GnRH as well as other GnRH isoforms and analogs with similar amino acid structure should exhibit the same or similar binding and bioactivity.

SUMMARY OF THE INVENTION

It is an object of the present invention to provide a novel pharmaceutical preparation that includes non-mammalian GnRH isoforms and their analogs specifically designed to bind to extra-pituitary GnRH receptors expressed on tumor tissues.

It is another object of the present invention to provide novel GnRH analogs that are resistant to degradation by post-proline peptidases, particularly those which are known to be found around tumor tissues.

Still another object of the present invention is to provide novel GnRH analogs that are resistant to the endopeptidase found circulating in the blood.

Another object of the present invention is to provide novel GnRH analogs that act as superagonists at the tumor tissue leading to tissue receptor down regulation.

Yet another object of the present invention is to provide novel GnRH analogs that act as pure antagonists of the endogenous form of GnRH in tumor tissue via the tumor tissue receptor.

Another object of the present invention is to provide novel GnRH analogs which reduce tumor cell proliferation.

Still another object of the present invention is to provide novel GnRH analogs which induce apoptosis.

It is yet another object of the present invention to provide novel GnRH analogs which reduce tumor cell metastasis.

Another object of the present invention is to provide novel GnRH analogs that can be used as anti-tumor agents.

Yet another object of the present invention is to provide novel GnRH analogs that can be used to reduce tumor cell growth.

It is still another object of the present invention to provide novel GnRH analogs that are stable in circulation.

Another object of the present invention is to provide novel GnRH analogs that are tumor tissue specific.

Yet another object of the present invention is to provide novel GnRH analogs which can be used to induce tumor regression.

Still another object of the present invention is to provide a novel method for synthesizing analogs of non-mammalian GnRH isoforms having increased activity in tumor tissues.

It is another object of the present invention to provide a novel method for inhibiting tumor growth which in turn reduces tumor cell proliferation, tumor size and metastasis i.e. apoptosis and tumor regression.

It is yet another object of the present invention to provide a novel method for using non-mammalian GnRH analogs directly on tumors as an anti-tumor or anti-metastasis drug.

Another object of the present invention is to provide a novel non-mammalian GnRH analog composed of Salmon, Chicken II, or Herring GnRH analogs that are modified at the C-terminal and which shown greater affinity for the tumor receptor than mammalian GnRH.

It is still another object of the present invention to provide a novel non-mammalian GnRH analog which has an aza-Gly-$NH_2$ substitution at the number 10 position to make the sequence more stable in tumor tissues and in blood and to inhibit degradation by post-proline peptidases.

Yet another object of the present invention is to provide a novel non-mammalian GnRH analog sequence which is substituted at the 6 position with preferably a D-Arg but could be any other D-amino acid such as, but not limited to, D-Leu, D-Trp, and D-Bu-Ser.

It is another object of the present invention to provide a novel non-mammalian GnRH analog which has increased binding affinity to the tumor receptor and metabolic stability.

Still another object of the present invention is to provide a novel non-mammalian GnRH analog which will not be toxic after long term therapies.

Yet another object of the present invention is to provide a novel more potent non-mammalian GnRH analog which can be used to bind to the tumor tissue GnRH receptor with high affinity so as to displace the endogenous GnRH-like activity and block its action.

It is another object of the present invention to provide a novel non-mammalian GnRH analog which incorporates a substitution of Gly(10)-$NH_2$ with ethylamide to inhibit degradation by post-proline peptidases.

Still another object of the present invention is to provide a novel non-mammalian GnRH analog which has minimal effect on the mammalian pituitary GnRH receptor.

In satisfaction of these and related objectives, Applicant's present invention provides unique non-mammalian peptide hormone analogs of non-mammalian GnRH and the method for use of these analogs in the regulation of cell growth, particularly tumor cell growth. Applicant's invention permits its practitioner to treat patients who have cancerous tumors with non-mammalian GnRH analogs which have high binding affinity to the GnRH receptors located on tumor cells which in turn reduces the tumor size and proliferation.

◇ GnRH 0.00313 M, ▽ GNRH 0.0625 M, ●GNRH 0.0125 M.

Figure 1:
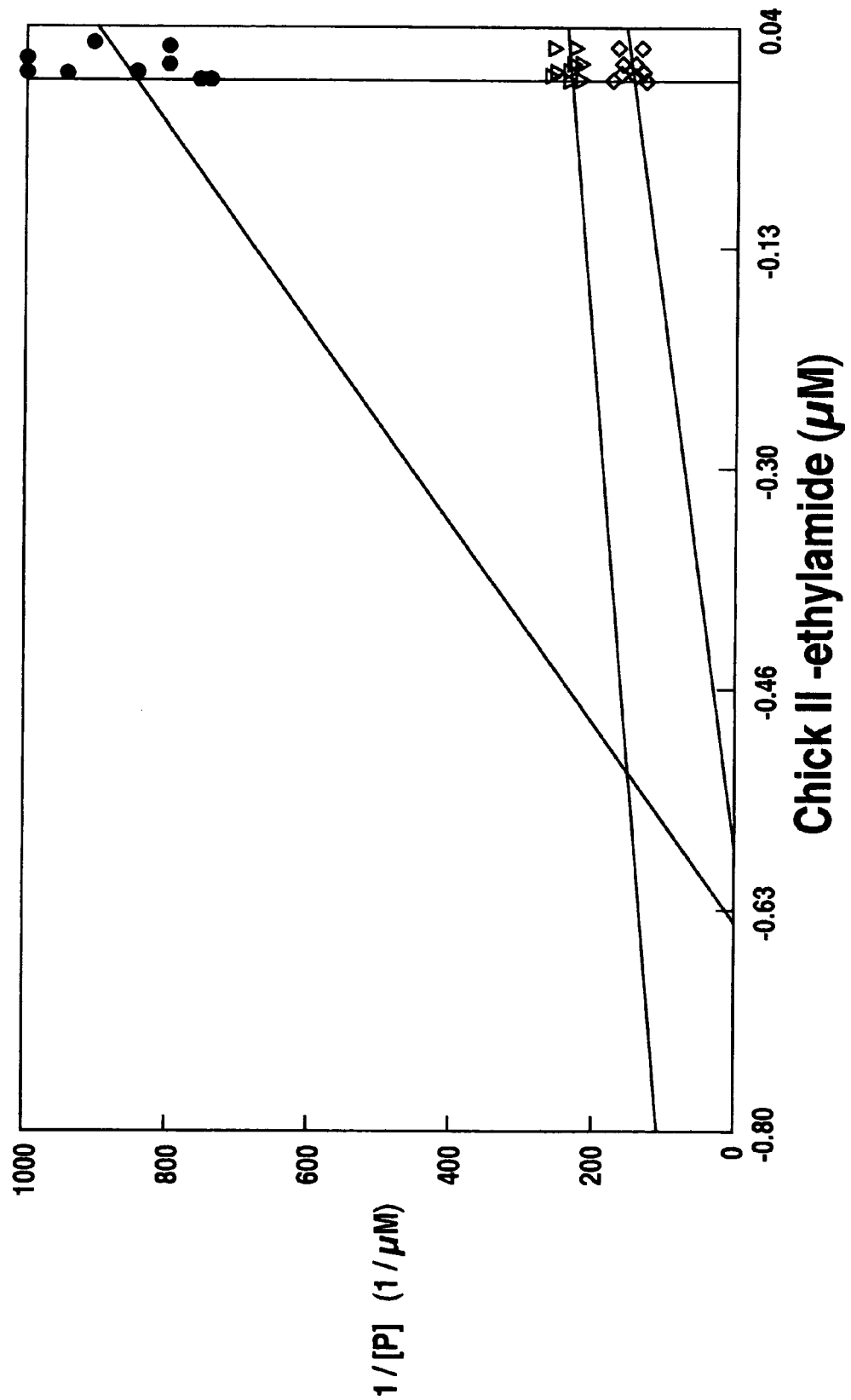
FIG. 1. Effect of des-Gly(10)-mammalian GnRH-ethylamide on the degradation of mammalian GnRH by the chorionic post-proline peptidase.
Figure 2:
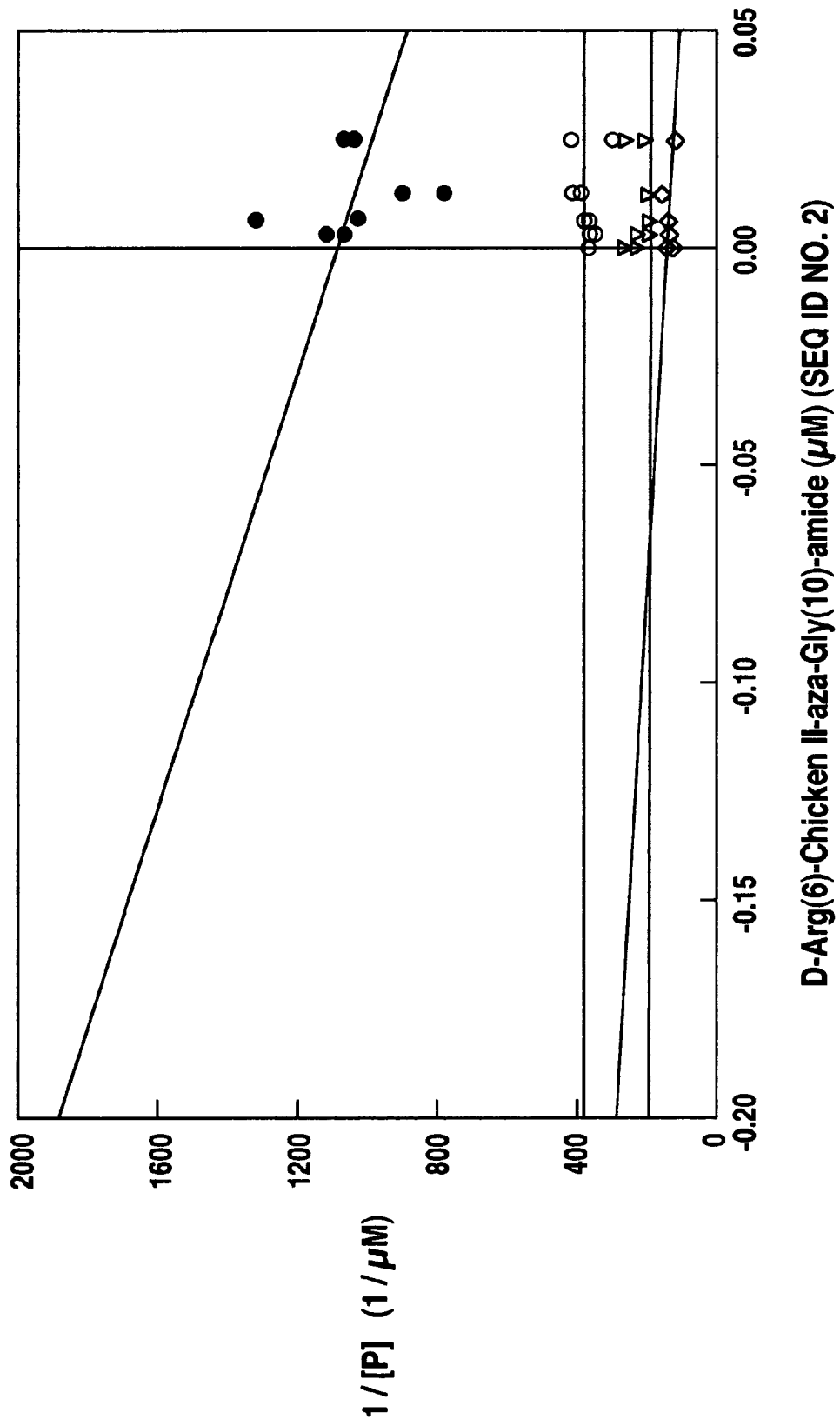

FIG. 2. Action of D-Arg-Chicken II-aza-Gly-$NH_2$ on the Degradation of Mammalian GnRH by Chorionic Post-Proline Peptidase. ◇ GnRH 0.00313 M, ▽ GNRH 0.0625 M, ●GNRH 0.0125 M, 0 GNRH 0.0250 M.

Figure 3:
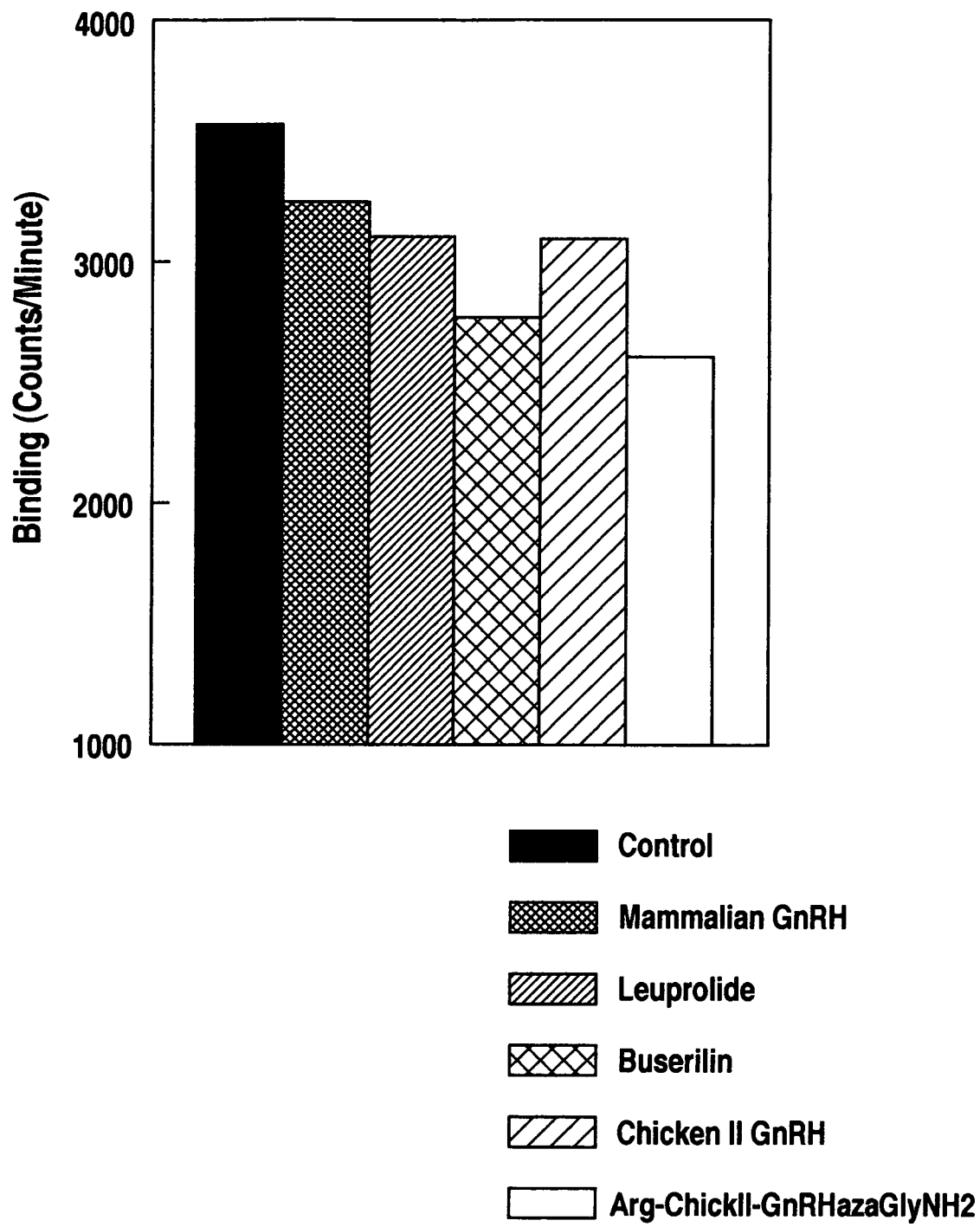

FIG. 3. Binding of $I^{125}$-D-Arg(6)-Chicken II GnRH-aza-Gly(10)-amide to MCF 7 breast cancer cells after 24 hours of incubation with no exogenous GnRH or competing isoforms or analogs of GnRH.

Figure 4:
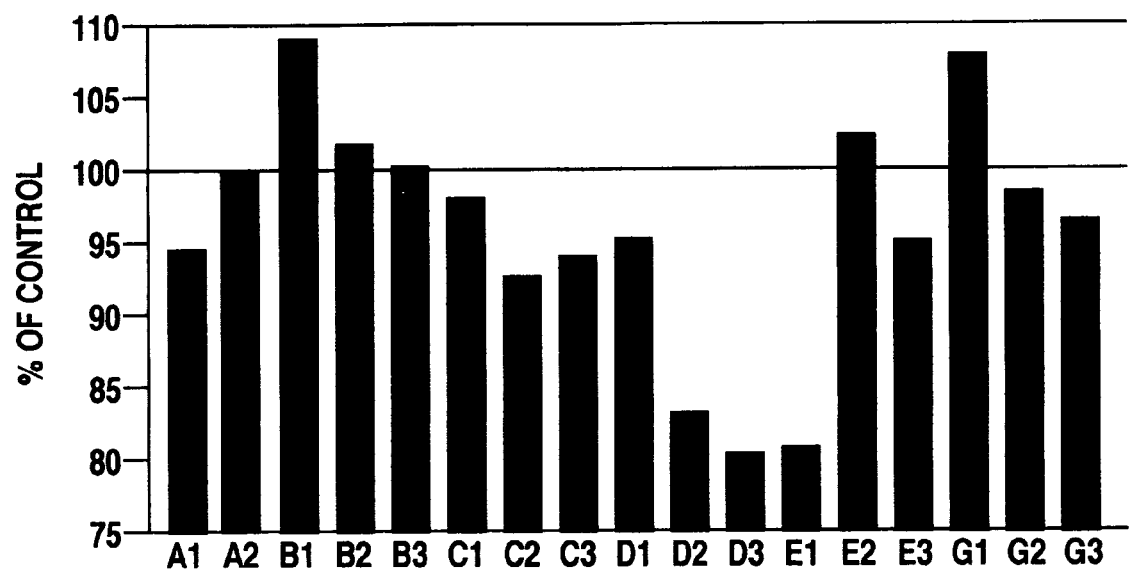

FIG. 4. The anti proliferative, tumor regression activity of D-Arg(6)-Chicken II GnRH-aza-Gly(10)-amide compared to controls and other isoforms and analogs of GnRH after 24 hours.

FIG. 5. Inhibitor constants for analogs of GnRH.

DETAILED DESCRIPTION OF THE PREFERRED EMBODIMENT

Following long-standing patent law convention, the terms "a" and "an" mean "one or more" when used in this application, including the claims.

It should be appreciated by those of skilled in the art that the techniques disclosed in the material which follows represent techniques discovered by the Applicants to function well in the practice of the invention, and thus can be considered to constitute preferred modes for its practice. However, those skilled in the art should, in light of the present disclosure, appreciate that many changes can be made in the specific embodiments which are disclosed and still obtain a like or similar result without departing from the spirit and scope of the invention.

Design & Synthesis of Non-Mammalian GnRH Analogs

The preferred embodiment for the present invention is the design of non-mammalian GnRH analogs that have increased activity in tumor tissue cells by exhibiting potent tumor receptor binding activity, tumor tissue stability, and biological activity.

Existing mammalian GnRH analogs are designed for activity at the pituitary GnRH receptor and with extended stability in the circulation of non-pregnant individuals i.e. protection from endopeptidase degradation. Yet, existing data indicate that the tumor GnRH receptor differs from that in the pituitary. Therefore, prior known pituitary mammalian GNRH analogs have not been designed for direct use in tumor tissues and potent non-mammalian GnRH analogs have not been designed for use to regulate cancer cell growth. The present invention provides potent non-mammalian GnRH analogs that act directly on tumor cell growth and proliferation.

Non-mammalian analogs of GnRH (SEQ ID NO: 2, SEQ ID NO: 4, and SEQ ID NO: 7) were designed according to general guidelines established by Applicants. First, these analogs were specifically designed to be resistant to degradation both in the maternal circulation as well as within the tumor tissue by endopeptidases and post-proline peptidases. This allows for the maintenance of sufficient concentrations of analog when administered via the maternal system to reach the cancerous tissue. And second, the analogs were designed according to the particular specificity of the tumor cell receptor to specifically bind the GnRH receptors with high affinity so as to preferably displace the endogenous GnRH activity and block its action. This tumor GnRH binding specificity can effect either a down regulation of the tumor GnRH receptor or act as a true antagonist to inhibit tumor growth, proliferation, and metastasis by inducing apoptosis and tumor regression by directly inhibiting tumor function.

Analogs of the Salmon and Chicken II GnRH sequences, that show greater affinity for the tumor GnRH receptor than for the pituitary GnRH receptor, were modified to the aza-Gly(10)-$NH_2$ analog to make them resistant to degradation by post-proline peptidases. Ethylamide or other similar amides can be used at position 10. Next, the Chicken II GnRH sequence (SEQ ID NO: 2 and SEQ ID NO: 7), and the Salmon GnRH sequence (SEQ ID NO: 4) were modified at the 6 position using D-Arg, D-Leu, D-tBu-Ser, D-Trp, or other similar amino acid making the analog resistant to degradation by the endopeptidase in blood, and at the 10 position using preferably aza-Gly(10)-$NH_2$, making it stable in maternal blood and the tumor tissues. Again, ethylamide or other similar amides can be used. These analogs are expected to have not only increased binding to the tumor receptor but also increased metabolic stability. Due to the similarity in amino acid makeup, these procedures could be repeated using Herring GnRH, Dogfish GnRH, and Catfish GnRH as well as any other decapeptide with similar amino acid structure. The preparation and chemical manipulation of these non-mammalian GnRH analogs can be completed with any standard protocol.

Tumor Receptor Binding of GnRH Isoforms and Analogs

The tumor receptor binding activity of the different non-mammalian GnRH analogs of the present invention was compared. Prior mammalian GnRH analogs have been designed to increase activity at the pituitary GnRH receptor and stability in the circulation of non-pregnant individuals. These analogs do not demonstrate as potent binding activity at the tumor receptor as they do at the pituitary receptor. In contrast and as was mentioned earlier, the non-mammalian GnRH analogs of the present invention have been designed to interact with preference at the tumor receptor and not the pituitary receptor.

GnRH receptors on the cells of MCF-7 breast cancer cells were studied. The cells were plated on 96 wells and grown to confluency in base medium (M3D:Fetal Bovine Serum [9:1]). Prior to the experiment the cells were down shifted to M3D: Fetal Bovine Serum [99:1] and then to serum-free medium. Cells were incubated for 24 hours at room temperature with mammalian GnRH, Buserilin, Leuprolide, Chicken II GnRH, and D-Arg(6) Chicken II-aza-Gly(10)-amide (SEQ ID NO: 2). Cells were then collected and studied for receptor binding and receptor number with D-Arg(6) Chicken II-aza-Gly(10)-amide (SEQ ID NO: 2). Addition of enzyme inhibitors of the endogenous post-proline peptidase and other peptidases were used as well as agents for receptor stabilization. Receptor bound label was separated by centrifugation. The binding of the non-mammalian GnRH analog and its ability to regulate the tumor cells' GnRH receptor was compared. FIG. 4 shows the binding of $I^{125}$-D-Arg(6)-Chicken II GnRH-aza-Gly (10)-amide to MCF-7 breast cancer cells after 24 hours of incubation with no exogenous GnRH or competing isoforms or analogs of GnRH. D-Arg(6)-Chicken II GnRH-aza-Gly (10)-amide (SEQ ID NO: 2) specifically bound the MCF-7 breast cancer cells. This binding was competitively inhibited by D-Arg(6)-Chicken II GnRH-aza-Gly(10)-amide (SEQ ID NO: 2) with the greatest potency. This was followed by Buserilin. Mammalian GnRH was the weakest competitor, while Chicken II GnRH was highly potent even though it is not protected from degradation either at the 6 or the 10 position. This indicated the high innate affinity of this isoform of GnRH for the tumor GnRH receptor. It is believed by Applicants that the same or similar results could be obtained using other non-mammalian GnRH isomers or analogs with similar amino acid structure as Chicken II GnRH such as but not limited to Salmon GnRH, Herring GnRH, Catfish GnRH, or Dogfish GnRH.

Tumor Tissue Stability Studies for GnRH Isoforms and Analogs

As has been previously mentioned, mammalian GnRH and its analogs bind with weak affinity to tumor cell receptors in certain tumor tissues whereas the non-mammalian GnRH analogs exhibit strong affinity for these receptors. Observing this strong affinity it became necessary to examine the non-mammalian GnRH analogs for stability. The non-mammalian GnRH analogs of the present invention have not previously been examined for stability. However, the added stability of these non-mammalian analogs would effect a substantial increase in bioactivity. Thus, stability studies involving endopeptidase and post-proline peptidase were performed for the non-mammalian GnRH analogs.

Endopeptidase Stability Studies:

Since human pituitary and blood contain an enzymatic activity that degrades GnRH at the 5-6 position, rather than the 9 position, present non-mammalian GnRH analogs have been designed to inhibit the former enzymatic activities and have substitutions in the 5-6 position of the molecule. The present analogs with these substitutions are therefore resistant to degradation at the pituitary or in the blood of non-pregnant individuals. However, these substitutions alone do not protect the analogs from degradation at the tumor tissues which contain post-proline peptidase. Substitution of the Gly (10)-$NH_2$ with ethylamide, or the more potent aza-Gly(10)-$NH_2$, inhibits degradation by post-proline peptidases. A number of existing mammalian GnRH analogs also have a substitution of Gly(10)-$NH_2$.

Post-Proline Peptidase Stability Studies: As mentioned earlier, the post-proline peptidase is important in actively degrading peptides that contain a proline residue. GnRH is such a peptide. Initially the enzymatic activity of the tumor cell was studied. Tumor tissue cells and their spent media were studied for enzyme activity. In particular, examination was made for the degradation of GnRH both with and without specific post-proline and endopeptidase activity inhibitors to determine the specificity of the tumor enzymatic activity. These studies have demonstrated very high post-proline peptidase activity produced by the tumor tissue.

The enzymatic degradation of the non-mammalian GnRH analogs (SEQ ID NO: 2, SEQ ID NO: 4 and SEQ ID NO: 7) were studied in MCF-7 breast cancer cells using an enzymatic activity assay and compared to that for the purified chorionic post-proline peptidase. Chorionic post-proline peptidase is a peptidase with high specificity for the degradation of GnRH at the proline-glycine bond, but can also degrade other GnRH species containing this bond.

In a non-pregnant individual very little post-proline peptidase activity is present in the blood or the pituitary. Thus, currently available mammalian GnRH analogs have not been designed to be resistant to degradation by this activity. However, due to the high post-proline peptidase activity present in tumor tissue, the non-mammalian GnRH analogs (SEQ ID NO: 2, SEQ ID NO: 4 and SEQ ID NO: 7) for cancer therapy described herein were designed to be resistant to this type of degradation. The stability of these non-mammalian GnRH analogs (SEQ ID NO: 2, SEQ ID NO: 4 and SEQ ID NO: 7) in the presence of post-proline homogenates was examined and compared to existing mammalian GnRH analogs. In addition, the ability of the analogs (SEQ ID NO: 2, SEQ ID NO: 4 and SEQ ID NO: 7) to competitively inhibit the degradation of GnRH using chorionic post-proline peptidase was studied.

The stability of most potent receptor-active non-mammalian GnRH analogs (SEQ ID NO: 2, SEQ ID NO: 4, and SEQ ID NO: 7) in the presence of tumor tissue cells, spent media, or tumor tissue cells homogenates was identified. Using the incubation system developed for chorionic post-proline peptidase activity, the degradation of GnRH was tested. Each of these analogs (SEQ ID NO: 2, SEQ ID NO: 4 and SEQ ID NO: 7) were first studied for their ability to act as a competitive inhibitor of GnRH for chorionic post-proline peptidase activity using the enzymatic activity assay as described previously (103). In this assay, incubation of enzyme and mammalian GnRH with and without the chosen newly synthesized non-mammalian GnRH analog (SEQ ID NO: 2, SEQ ID NO: 4 and SEQ ID NO: 7) was studied. The reaction was stopped by heating at 85° C. for 10 minutes. The remaining mammalian GnRH substrate was quantified by radioimmunoassay. The product formed, i.e. the N-terminal nonapeptide of GnRH, was calculated by subtraction, and its inverse plotted against the inverse of the original substrate concentrations to determine the Ks of the competition. The Ki was determined by plotting the inverse of the product that formed versus the inhibitor used. The inhibitory activity of Antide, Im-btl-D-His(6)-mammalian-GnRH-ethylamide, D-Trp(6)-GnRH-ethylamide, Buserilin, Leuprolide, OH-Pro(9)-Mammalian GnRH, Mammalian GnRH-ethylamide, Chicken II GnRH, Chicken II-ethylamide, D-Arg(6)-Chicken II-ethylamide (SEQ ID NO: 2), D-Arg(6)-Chicken II-aza-Gly(10)-amide (SEQ ID NO: 2), Chicken I GnRH, Salmon GnRH, D-Arg (6)-Salmon GnRH-aza-Gly(10)-amide (SEQ ID NO: 4), and Lamprey GnRH was studied.

Mammalian GnRH was actively degraded by chorionic post-proline peptidase. While replacement of Gly(10)-NH$_2$ with ethylamide made each of the mammalian GnRH analogs more resistant to degradation than Mammalian GnRH alone, some of these Mammalian GnRH were still degraded by the post-proline peptidase. Of four mammalian GnRH ethylamides studied, des-Gly(10)-GnRH ethylamide, des-Gly(10), D-Trp(6)-GnRH ethylamide, des-Gly(10)-D-Leu(6)-GnRH ethylamide, and Buserilin, each competitively inhibited the degradation of mammalian GnRH; thus they were degraded by the post-proline peptidase. The effect of des-Gly(10) GnRH on the degradation of mammalian GnRH by chorionic post-proline peptidase is shown in FIG. 2. The less an analog is capable of competing with the GnRH for the post-proline peptidase, the more resistant it is to degradation by post-proline peptidase and the more stable the analog will be in the tumor tissue and/or in the blood. Thus the existing mammalian GnRH analogs commonly used in medicine can be degraded in tumor tissues.

This activity of chorionic post-proline peptidase was inhibited by OH-Pro(9)-GnRH, Lamprey GnRH, Chicken I GnRH, Antide, Chicken II GnRH, and Salmon GnRH with relative potency of 1.5, 1.5, 0.6, 0.6, 0.2, and 0.2, respectively, compared to that for GnRH. In viewing this data, the OH-Pro (9)-GnRH and Lamprey GnRH were determined to be the best competitors for GnRH degradation by chorionic post-proline peptidase. (See FIG. 5 for inhibitor constants for analogs of GnRH.) They are as or even more potent than mammalian GnRH. Antide and Chicken I GnRH are three fold less potent than GnRH, but two fold more potent than the Salmon GnRH or Chicken II GnRH. The addition of ethylamide to mammalian GnRH, both with and without the D-Trp (6)-, D-Phe(6) substitution, decreased the competition with mammalian GnRH for chorionic post-proline peptidase degradation, but not as markedly as did the Im-btl-D-His(6) or Chicken II GnRH analogs. Both D-Arg(6)-Chicken II GnRH-aza-Gly(10)-amide (SEQ ID NO: 2) and Im-btl-D-His(6)-GnRH-ethylamide were essentially inactive, i.e. <0.005 inhibitory activity for GnRH. Essentially these latter two GnRH's were greater than 200 fold less active in the inhibition of GnRH degradation by chorionic post-proline peptidase. Thus these analogs appear to be very stable in the presence of post proline peptidase activity, however the Im-btl-His(6) analog has reduced receptor potency. The stability of the D-Arg (6)-Chicken II GnRH-aza-Gly(10)-amide (SEQ ID NO: 2) was found to not only to be greater than 200 fold more stable than GnRH but it still has increased receptor potency. The action of D-Arg(6)-Chicken II GnRH-aza-Gly (10)-amide (SEQ ID NO: 2) on the degradation of mammalian GnRH by chorionic post-proline peptidase is shown in FIG. 2. It is believed by Applicants that the same or similar results could be obtained using non-mammalian GnRH isomers or analogs with similar amino acid structure as Chicken II GnRH such as but not limited to Herring GnRH, Dogfish GnRH, or Catfish GnRH.

Since chorionic post-proline peptidase is a peptidase with high specificity for the degradation of GnRH at the proline-glycine peptide bond it can also degrade other GnRH species containing the same bond. The synthetic mammalian GnRH analogs such as Antide are degraded with reduced activity while other analogs such as D-Arg(6)-Chicken II GnRH-aza-Gly(10)-amide (SEQ ID NO: 2) are resistant to degradation by this endogenous chorionic enzyme. Such a resistant analog can be useful in the regulation of tumor tissue GnRH activity.

Degradation of mammalian GnRH by the tumor tissue cells was essentially 100% after overnight incubation. Specific inhibitors of post-proline peptidase were used to demonstrate this activity in the tumor cell extracts. The degradation of mammalian GnRH was inhibited by bacitracin, but not EDTA, demonstrating the enzyme similarity to chorionic post proline peptidase. From this study it was found that the aza-Gly(10)amide derivatives of Chicken II GnRH and Salmon GnRH have little if any degradation as compared to mammalian GnRH. Each Chicken II and its analogs were more stable than the mammalian GnRH analogs analyzed. It is believed by Applicants that the same or similar results could be obtained using non-mammalian GnRH isomers or analogs with similar amino acid structure as Chicken II GnRH such as but not limited to Herring GnRH, Dogfish GnRH, or Catfish GnRH.

Although the enzyme competition system had already been developed, newly synthesized non-mammalian GnRH analogs have not been utilized in this system. Previous data generated by Applicants have demonstrated that the antiserum is specific for mammalian GnRH, thus reducing potential for cross-reaction of non-mammalian GnRH isoforms or its analogs in the assay used in these studies.

Biological Activity Studies

The tumor growth inhibiting activity of the non-mammalian GnRH analogs was studied. Such data can be used to determine biological activity including regulation of tumor cell growth, tumor proliferation, and tumor regression. Biopotency was studied by determining cell death and tumor regression. Thus a primary parameter of interest was indicating the cell viability in the tumor cells being regulated by the exogenous GnRH activities which were studied.

The biological activity of the newly synthesized non-mammalian GnRH analogs (SEQ ID NO: 2, SEQ ID NO: 4, and SEQ ID NO: 7) was studied using an in vitro human tumor cell culture system. This system allows for replicated extended activity studies. Mammalian GnRH action on the tumor tissue cell has been studied using a similar system. Applicants studied replicate cultures, thus allowing for comparison of different doses of each non-mammalian GnRH analog (SEQ ID NO: 2, SEQ ID NO: 4 and SEQ ID NO: 7) to mammalian GnRH. In these studies, the action of the most stable and receptor-active non-mammalian GnRH analogs (SEQ ID NO: 2, SEQ ID NO: 4 and SEQ ID NO: 7) on tumor cell viability were determined.

The bio-potency studies were done with a MCF-7 breast cancer cell culture system and the cell viability as a measure of survival was assessed using the Alamar Blue assay. The percent difference in the Alamar Blue optical density (OD) readings at 570 and 600 nm in the treated and untreated controls was determined. These studies were done using mammalian GnRH, chicken II GnRH, Leuprolide, Buserelin, the D-Arg(6)-Chicken II GnRH-aza-Gly(10)-amide analog (SEQ ID NO: 2) as well as the D-Leu(6)-Chicken II GnRH-aza-Gly(10)-amide analog. A dose-response study in quadruplicate cultures was performed. Cell viability was assessed after 24 and 48 hours of incubation with the activity agent. The data analysis of these tumor cell culture sets at 24 hours is shown in FIG. 5.

More specifically, FIG. 5 illustrates the anti-proliferative, tumor regression activity of D-Arg(6)-Chicken II GnRH-aza-Gly(10)-amide (SEQ ID NO: 2) as compared to controls and other isoforms and analogs of GnRH after 24 hours of incubation. In this FIG. 5, A1 is medium 199 (no vehicle); A2 is medium 199 (with vehicle); B1-B3 is Leuprolide; C1-C3 is mammalian GnRH; D1-D3 is Chicken II GnRH; E1-E3 is D-Arg(6)-Chicken II GnRH-aza-Gly(10) amide (SEQ ID NO: 2); G1-G3 is Buserelin.

After 24 hours of incubation, an inhibition of cell proliferation was observed with the Chicken II GnRH and its analogs, while even the highest doses of mammalian GnRH analogs, Leuprolide, and Buserelin were totally inactive. (See FIG. 5). The lowest dose of Chicken II studied ($10^{-8}$ M) was more effective than $10^{-5}$ M mammalian GnRH. The D-Arg (6)-Chicken II GnRH-aza-Gly(10)-amide (SEQ ID NO: 2) resulted in positive dose-related activity, which was markedly active at $10^{-5}$ M. After 48 hours of incubation this analog was equally as potent as at 24 hours, while its natural isoform lost potency due to degradation. The mammalian GnRH and its analogs were totally ineffective in the inhibition of the MCF-7 breast cancer cell proliferation after 48 hours of continued exposure. These data demonstrate that D-Arg(6)-Chicken II GnRH-aza-Gly(10)-amide analog (SEQ ID NO: 2) is a very stable and bioactive molecule in the regulation of tumor cell growth in the human MCF-7 breast cancer cells. It is believed by Applicants that the same or similar results could be obtained using non-mammalian GnRH isomers or analogs with similar amino acid structure to Chicken II GnRH such as but not limited to Salmon GnRH, Herring GnRH, Dogfish GnRH, or Catfish GnRH.

Using an in vitro system to define bio-potency is expected to be predictive of in vivo activity. In addition to tumor cell action, since these newly synthesized non-mammalian GnRH analogs are known to act directly at the placenta to inhibit steroidogenesis, these analogs are expected to be active at the ovarian level to inhibit steroidogenesis. This would act as an added benefit in the cancer therapy.

Methods for Regulating Tumor Cell Growth and Proliferation In Vivo

In vivo trials utilizing the non-mammalian GnRH analogs (SEQ ID NO: 2, SEQ ID NO: 4 and SEQ ID NO: 7) of the present invention may be performed to inhibit tumor cell growth and proliferation to thus induce regression of cancer cells in a mammal. The mammal can include a human with cancer. As a proposed dose regimen, it is anticipated that a human between 100 lbs. and 250 lbs. be administered about 10 nanograms to 1.0 gram of a chicken II GnRH analog (SEQ ID NO: 2), salmon GnRH analog (SEQ ID NO: 4), or other non-mammalian GnRH analog with similar amino acid structure. This would be expected to be effective for inhibiting tumor growth or metastasis in the mammal once administered.

It is envisioned that these non-mammalian GnRH analogs (SEQ ID NO: 2, SEQ ID NO: 4 and SEQ ID NO: 7) will be administered intra-nasally, orally, intramuscularly, transdermally or vaginally. However, virtually any mode of administration may be used in the practice of the invention. Treatment with these analogs may require short-term, repeated administrations of the active non-mammalian GnRH analog (SEQ ID NO: 2, SEQ ID NO: 4 and SEQ ID NO: 7) or long-term continuous therapy until tumor regression has occurred. Repeated administration could be used as needed.

Numerous in vitro fertilization (IVF) protocols now routinely use mammalian GnRH analogs for ovulation timing and have been shown to be nontoxic, even after weeks of administration. Long-term therapies with mammalian GnRH analogs have been used for treatment of endometrious, prostate cancer and other cancers and have been shown to be nontoxic, even after months of administration. Long-term therapies with mammalian GnRH analogs have been associated with a hypoestrogenic state, which is frequently a desired condition in certain cancer therapies. The effect on the pituitary GnRH receptor is expected to be minimal with these non-mammalian GnRH analogs (SEQ ID NO: 2, SEQ ID NO: 4 and SEQ ID NO: 7) and with this short duration of treatment. Thus, the specific receptor activity of these analogs makes it less likely to interfere with normal physiology.

In some trials, the dosing regimen can comprise a pulsatile administration of the analog over a 24-hour period, wherein the daily dosage is administered in relatively equal ½4th fractions. For example, where the daily dose is about 2.4 micrograms, the patient would be administered about 0.1 micrograms per hour over a 24-hour period. Such a daily pulsatile administration would create a hormonal environment in the patient sufficient to inhibit tumor cell growth and proliferation and/or induce its regression. The particular pharmaceutical preparations may be created by one of skill in the pharmaceutical arts. Remington's Pharmaceutical Sciences Remington: The Science and Practice of Pharmacy, 19"

Antibodies Specific for Non-Mammalian GNRH

Another embodiment of the present invention is to utilize non-mammalian GnRH analogs to prepare antibodies that preferentially bind the non-mammalian GnRH peptide sequences, or that bind the tumor tissues or any other non-pituitary GnRH peptide or protein. It is anticipated that these non-mammalian GnRH antibodies may be used in a variety of screening assays. For example, these antibodies may be used to determine levels of GnRH are present in a sample as an indicator molecule. The levels of such GnRH may be used to monitor and follow a patient's tumor activity or growth, as well as an indicator of the tumor's presence. The antibodies to non-mammalian GnRH may be monoclonal or polyclonal antibodies.

Polyclonal antibodies may be created by standard immunization techniques, wherein the immunogen used will be the non-mammalian chicken II GnRH, salmon GnRH, herring GnRH analog, or the naturally occurring decapeptide of any of these described herein, or any other non-mammalian GnRH analog with similar amino acid structure. These peptides may be used either alone or together in a pharmaceutically acceptable adjuvant. The animal, such as a rabbit, would be administered several doses of the decapeptide preparation, and the levels of the animal's antibody blood levels monitored until an acceptable antibody level (titer) had been reached.

For the preparation of monoclonal antibodies, one would follow standard techniques for the immunization of an animal, again using the decapeptide non-mammalian GnRH peptide or its analog. Once sufficiently high acceptable antibodies are reached (titer) in the animal, the spleen of the animal would be harvested and then fused with an immortalized cell line, such as a cancer cell line, to produce a population of hybridoma cells. This hybridoma population of cells would then be screened for those cells that produce the highest amount of antibody that specifically binds the non-mammalian GnRH analog decapeptide. Such hybridoma cells would be selected, and then cultured. The antibody to non-mammalian GnRH would then be collected from the media of the cell culture using techniques well known to those of skill in the art.

For purposes of the practice of preparing polyclonal and monoclonal antibody, the textbook Sambrook et al (1989) *Molecular Cloning, A Laboratory Manual*, @d Ed., Cold Springs Harbor Laboratory, Cold Springs Harbor, N. Y., is specifically incorporated herein by reference. In addition to the embodiments presented it is believed by Applicants that the disclosed non-mammalian GnRH isomers and/or analogs as well as any other gene regulator can be used to regulate the gene expression of non-mammalian GnRH or expression of its receptors in tumor cells. It is further believed by Applicants that the non-mammalian GnRH analogs (SEQ ID NO: 2, SEQ ID NO: 4, and SEQ ID NO: 7) disclosed can be used in the development of stable, toxin conjugated antibodies or ligands that can specifically bind to the GnRH receptor on the tumor cell and kill the cell.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described therein without departing from the concept, spirit and scope of the invention. More specifically, it will be apparent that certain agents, who are both chemically and physiologically, related, might be substituted for the agents described herein while the same or similar results would be achieved. All such similar substitutes and modifications apparent to those skilled in the art are deemed to be within the spirit, scope and concept of the invention as defined by the appended claims.

REFERENCES

1. Burgus R, Guillemin R 1970 Hypothalamic releasing factors. Ann Rev Biochem 39:499-526
2. Baba Y, Matsuo H, Schally A V 1971 Structure of the porcine LH- and FSH-releasing hormone. II. Confirmation of the proposed structure by conventional sequential analyses. Biochem Biophys Res Commun 44:459-463
3. Corbin A 1982 From contraception to cancer: A review of the therapeutic applications of LHRH analogues as antitumor agents. Yale J Biol Med 55:27-47
4. Buzdar A U, Hortobagyi G 1998 Update on endocrine therapy for breast cancer. Clin Cancer Res 4:527-534
5. Bare, R. L. and F. M. Torti. 1998. Endocrine therapy of prostate cancer. In Biological and hormonal therapies of cancer. K. A. Foon and H. B. Muss, editors. Kluwer Academic Publishers, Boston. 69-86.
6. Siler-Khodr T M, Khodr G S 1978 Luteinizing hormone releasing factor content of the human placenta. Am J Obstet Gynecol 130:216-219
7. Khodr G S, Siler-Khodr T M 1978 Localization of luteinizing hormone releasing factor (LRF) in the human placenta. Fert Steril 29:523-526
8. Siler-Khodr T M, Khodr G S 1979 Extrahypothalamic luteinizing hormone releasing factor (LRF): Release of immunoreactive LRF by the human placenta in vitro. Fert Steril 22:294-296
9. Khodr G S, Siler-Khodr T M 1980 Placental LRF and its synthesis. Science 207:315-317
10. Siler-Khodr, T. M. 1992. The Placenta: Part IV-Function of the Human Placenta. In Neonatal and Fetal Medicine. R. A. Polin and W. W. Fox, editors. W.B. Saunders Co. Philadelphia, Pa. 74-86.
11. Youngblood W W, Humm J, Kizer J S 1979 TRH-like immunoreactivity in rat pancreas and eye, bovine and sheep pineals, and human placenta: Non-identity with synthetic Pyroglu-His-Pro-NH2 (TRH). Brain Res 163:101-110
12. Dubois M P 1975 Immunoreactive somatostatin is present in discrete cells of the endocrine pancreas. Proc Natl Acad Sci USA 72:1340-1343
13. Adashi, E. Y. 1996. The Ovarian Follicular Apparatus. In Lippincott-Raven Publishers. E. Y. Adashi, J. A. Rock, and Z. Rosenwaks, editors. Lippincott-Raven Publishers, Philadelphia. 17-40.
14. Szende B, Srkalovic G, Groot K, Lapis K, Schally A V 1990 Growth inhibition of mouse MXT mammary tumor by the luteinizing hormone-releasing hormone antagonist SB-75. J Natl Cancer Inst 82:513-517
15. Srkalovic G, Wittliff J L, Schally A V 1990 Detection and partial characterization of receptors of [D-Trp(6)]-luteinizing hormone-releasing hormone and epidermal growth factor in human endometrial carcinoma. Cancer Res 50:1841-1846
16. Szende B, Srkalovic G, Groot K, Lapis K, Schally A V 1991 Regression of nitrosamine-induced pancreatic cancers in hamsters treated with luteinizing hormone-releasing hormone antagonists or agonists. Cancer Res 50:3716-3721
17. Ohno T, Atsushi I, Furui T, Takahashi K, Tamaya T 1993 Presence of gonadotropin-releasing hormone and its messenger ribonucleic acid in human ovarian epithelial carcinoma. Am J Obstet Gynecol 169:605-610
18. Palyi I, Vincze B, Kalnay A, Turi G, Mezo I, Teplan I, Seprodi J, Pato J, Mora M 1996 Effect of gonadotropin-releasing hormone analogs and their conjugates on gonadotropin-releasing hormone receptor-positive human cancer cell lines. Cancer Detect Prey 20:146-152
19. Teissmann T, Klenner T, Deger W, Hilgard P, McGregor G P, Voigt K, Engel J 1996 Pharmacological studies with cetrorelix (SB-75), a potent antagonist of luteinising hormone-releasing hormone. Eur J Cancer 32A:1574-1579
20. Chatzaki E, Bax M R, Eidne K A, Anderson L, Grudzinskas J G, Gallagher C J 1996 The expression of gonadodtropin-releasing hormone and its receptor in endometrial cancer, and its relevance as an autocrine growth factor. Cancer Res 56:2059-2065
21. Jungwirht A, Galvan G, Pinski J, Halmos G, Szepeshazi K, Cai R Z, Groot K, Schally A V 1997 Luteinizing hormone-releasing hormone antagonist cetrorelix (SB-75) and bombesin antagonist RC-3940-II inhibit the growth of androgen-independent PC-3 prostate cancer in nude mice. Prostate 32:164-172
22. Jungwirth A, Pinski J, Galvan G, Halmos G, Szepeshazi K, Cai R Z, Groot K, Vadillo-Buenfil M, Schally A V 1997 Inhibition of growth of androgen-independent DU-145 prostate cancer in vivo by luteinising hormone-releasing hormone antagonist cetrorelix and bombesin antagonists RC-3940-II and RC-3950-II. Eur J Cancer 33:1141-1148
23. Bahk J Y, Hyun J S, Lee H, Kim M O, Cho G J, Lee B H, Choi W S 1998 Expression of gonadotropin-releasing hormone (GnRH) and GnRH receptor mRNA in prostate cancer cells and effect of GnRH on the proliferation of prostate cancer cells. Urol Res 26:259-264
24. Van Groeninghen J C, Kiesel L, Winkler D, Zwirner M 1998 Effect of luteinising-hormone-releasing hormone on nervous-system tumors. Lancet 352:372-373
25. Yin H, Cheng K W, Hwa H, Peng C, Auersperg N, Leung P C K 1998 Expression of the messenger RNA for gonadotropin-releasing hormone and its receptor in human cancer cell lines. Life Sci 62:2015-2023
26. Lamharzi N, Schally A V, Koppan M 1998 Luteinizing hormone-releasing hormone (LH-RH) antagonist Cetrorelix inhibits growth of DU-145 human androgen-independent prostate carcinoma in nude mice and suppresses the levels and mRNA expression of IGF-II in tumors. Regul Pept 77:185-192
27. Brewer C A, Shevlin D 1998 Encouraging response of an advanced steroid-cell tumor to GnRH agonist therapy. Obstet Gynecol 92:661-663
28. Mesia A F, Williams F S, Yan Z, Mittal K 1998 Aborted leiomyosarcoma after treatment with leuprolide acetate. Obstet Gynecol 92:664-666
29. Motomura S 1998 Inductions of apoptosis in ovarian carcinoma cell line by gonadotropin-releasing hormone agonist. Kurume Med J 45:27-32
30. Imai A, Takagi A, Horibe S, Takagi H, Tamaya T 1998 Fas and Fas ligand system may mediate antiproliferative activity of gonadotropin-releasing hormone receptor in endometrial cancer cells. Int J Oncol 13:97-100
31. Lamharzi N, Halmos G, Jungwirth A, Schally A V 1998 Decrease in the level and mRNA expression of LH-RH and EGF receptors after treatment with LH-RH anatagonist Cetrorelix in DU-145 prostate tumor xenografts in nude mice. Int J Oncol 13:429-435
32. Sherwood N M, Lovejoy D A, Coe I R 1993 Origin of mammalian gonadotropin-releasing hormones. Endocr Rev 14:241-254
33. King J A, Millar R P 1995 Evolutionary aspects of gonadotropin-releasing hormone and its receptor. Cell Mol Neurobiol 15:5-23
34. Siler-Khodr T M, Khodr G S, Valenzuela G 1984 Immunoreactive gonadotropin-releasing hormone level in maternal circulation throughout pregnancy. Am J Obstet Gynecol 150:376-379
35. Sorem K A, Smikle C B, Spencer D K, Yoder B A, Grayson M A, Siler-Khodr T M 1996 Circulating maternal CRH and GnRH in normal and abnormal pregnancies. Am J Obstet Gynecol 175:912-916
36. Khodr G S, Siler-Khodr T M 1979 The effect of luteinizing hormone releasing factor (LRF) on hCG secretion. Fert Steril 30:301-304
37. Siler-Khodr T M, Khodr G S 1981 Dose response analysis of GnRH stimulation of hCG release from human term placenta. Biol Reprod 25:353-358
38. Siler-Khodr T M, Khodr G S, Valenzuela G, Rhode J 1986 Gonadotropin-releasing hormone effects on placental hormones during gestation: I. Alpha-human chorionic gonadotropin, human chorionic gonadotropin and human chorionic somatomammotropin. Biol Reprod 34:245-254
39. Siler-Khodr T M, Khodr G S, Valenzuela G, Harper M J, Rhode J 1986 GnRH effects on placental hormones during gestation. III. Prostaglandin E, prostaglandin F, and 13,14-dihydro-15-keto-prostaglandin F. Biol Reprod 35:312-319
40. Kang I S, Koong M K, Forman J S, Siler-Khodr T M 1991 Dose-related action of GnRH on basal prostanoid production from the human term placenta. The 38th Annual Meeting of the Society for Gynecologic Investigation (San Antonio) Abstract #310:253(Abstr.)
41. Siler-Khodr T M, Khodr G S, Harper M J, Rhode J, Vickery B H, Nestor J J, Jr. 1986 Differential inhibition of human placental prostaglandin release in vitro by a GnRH antagonist. Prostaglandins 31:1003-1010
42. Siler-Khodr, T. M. and G. S. Khodr. 1981. The production and activity of placental releasing hormones. In Fetal Endocrinology. J. Resko and W. Montagna, editors. Academic Press, Inc. New York. 183-210.
43. Siler-Khodr, T. M. and G. S. Khodr. 1982. GnRH in the placenta. In Role of Peptides and Proteins in Control of Reproduction. D. S. Dhindsa and S. M. McCann, editors. Elsevier North Holland, New York. 347-363.
44. Siler-Khodr T M 1983 Hypothalamic-like releasing hormones of the placenta. Clin Perinatol 10:553-566
45. Siler-Khodr T M 1983 Hypothalamic-like peptides of the placenta. Semin Reprod Endocrinol 1:321-333
46. Shi L Y, Zhang Z W, Li W X 1994 Regulation of human chorionic gonadotropin secretion and messenger ribonucleic acid levels by follistatin in the NUCC-3 choriocarcinoma cell line. Endocrinology 134:2431-2437
47. Steele G L, Currie W D, Yuen B H, Jia X C, Perlas E, Leung P C 1993 Acute stimulation of human chorionic gonadotropin secretion by recombinant human activin-A in first trimester human trophoblast. Endocrinology 133: 297-303
48. Li W, Olofsson J I, Jeung E B, Krisinger J, Yuen B H, Leung P C 1994 Gonadotropin-releasing hormone (GnRH) and cyclic AMP positively regulate inhibin subunit messenger RNA levels in human placental cells. Life Sci 55:1717-1724

49. Petraglia F, Vaughan J, Vale W 1991 Inhibin and activin modulate the release of gonadotropin-releasing hormone, human chorionic gonadotropin, and progesterone from cultured human placental cells. Proc Natl Acad Sci USA 86:5114-5117
50. Petraglia F, Sawchenko P, Lim A T W, Rivier J, Vale W 1987 Localization, secretion, and action of inhibin in human placenta. Science 237:187-189
51. Shi C Z, Zhuang L Z 1993 Norepinephrine regulates human chorionic gonadotrophin production by first trimester trophoblast tissue in vitro. Placenta 14:683-693
52. Cemerikic B, Maulik D, Ahmed M S 1992 Opioids regulation of hCG release from trophoblast tissue is mediated by LHRH. Placenta Abstract:9(Abstr.)
53. Petraglia F, Vaughan J, Vale W 1990 Steroid hormones modulate the release of immunoreactive gonadotropin-releasing hormone from cultured human placental cells. J Clin Endocrinol Metab 70:1173-1178
54. Haning R V, Jr., Choi L, Kiggens A J, Kuzma D L, Summerville J W 1982 Effects of dibutyryl adenosine 3',5'-monophosphate, luteinizing hormone-releasing hormone, and aromatase inhibitor on simultaneous outputs of progesterone 17b-estradiol, and human chorionic gonadotropin by term placental explants. J Clin Endocrinol Metab 55:213-218
55. Petraglia F, Lim A T, Vale W 1987 Adenosine 3',5'-monophosphate, prostaglandins, and epinephrine stimulate the secretion of immunoreactive gonadotropin-releasing hormone from cultured human placental cells. J Clin Endocrinol Metab 65:1020-1025
56. Haning R V, Jr., Choi L, Kiggens A J, Kuzma D L 1982 Effects of prostaglandins, dibutyryl camp LHRH, estrogens, progesterone, and potassium on output of prostaglandin F2a, 13,14-dihydro-15-keto-prostaglandin F2a, hCG, estradiol, and progesterone by placental minces. Prostaglandins 24:495-506
57. Barnea E R, Feldman D, Kaplan M 1991 The effect of progesterone upon first trimester trophoblastic cell differentiation and human chorionic gonadotrophin secretion. Hum Reprod 6:905-909
58. Barnea E R, Kaplan M 1989 Spontaneous, gonadotropin-releasing hormone-induced, and progesterone-inhibited pulsatile secretion of human chorionic gonadotropin in the first trimester placenta in vitro. J Clin Endocrinol Metab 69:215-217
59. Branchaud C, Goodyer C, Lipowski L 1983 Progesterone and estrogen production by placental monolayer cultures: Effect of dehydroepiandrosterone and luteinizing hormone-releasing hormone. J Clin Endocrinol Metab 56:761-766
60. Ahmed N A, Murphy B E 1988 The effects of various hormones on human chorionic gonadotropin production in early and late placental explant cultures. Am J Obstet Gynecol 159:1220-1227
61. Iwashita M, Watanabe M, Adachi T, Ohira A, Shinozaki Y, Takeda Y, Sakamoto S 1989 Effect of gonadal steroids on gonadotropin-releasing hormones stimulated human chorionic gonadotropin release by trophoblast cells. Placenta 10:103-112
62. Haning R V, Jr., Choi L, Kiggens A J, Kuzma D L, Summerville J W 1982 Effects of dibutyryl cAMP, LHRH, and aromatase inhibitor on simultaneous outputs of prostaglandin F2a, and 13,14-dihydro-15-keto-prostaglandin F2a by term placental explants. Prostaglandins 23:29-40
63. Wilson E, Jawad M 1980 Luteinizing hormone-releasing hormone suppression of human placental progesterone production. Fert Steril 33:91-93
64. Duello T M, Tsai S J, Van Ess P J 1993 In situ demonstration and characterization of progonadotropin-releasing hormone messenger ribonucleic acid in first trimester human placentas. Endocrinology 133:2617-2623
65. Kelly A C, Rodgers A, Dong K W, Barrezueta N X, Blum M, Roberts J L 1991 Gonadotropin-releasing hormone and chorionic gonadotropin gene expression in human placental development. DNA Cell Biol 10:411-421
66. Berry S A, Pescovitz O H 1988 Identification of a rat GHRH-like substance and its messenger RNA in rat testis. Endocrinology 123:661-663
67. Radovick S, Wondisford F E, Nakayama Y, Yamada M, Cutler G B, Jr., Weintraub B D 1990 Isolation and characterization of the human gonadotropin-releasing hormone gene in the hypothalamus and placenta. Mol Endocrinol 4:476-480
68. Adelman J P, Mason A J, Hayflick J S, Seeburg P H 1986 Isolation of the gene and hypothalamic cDNA for the common precursor of gonadotropin-releasing hormone and prolactin release-inhibiting factor in human and rat. Proc Natl Acad Sci USA 83:179-183
69. Rakoff J, VandenBerg G, Siler T M, Yen S S C 1973 An integrated direct functional test of the adenohypophysis. The Pacific Coast Obstetrics and Fertility Society, Las Vegas (Abstract):(Abstr.)
70. Dong K W, Yu K L, Roberts J L 1993 Identification of a major up-stream transcription start site for the human progonadotropin-releasing hormone gene used in reproductive tissues and cell lines. Mol Endocrinol 7:1654-1666
71. Dong K W, Duval P, Zeng Z, Gordon K, Williams R F, Hodgen G D, Jones G, Kerdelhue B, Roberts J L 1996 Multiple transcription start sites for the GnRH gene in rhesus and cynomolgus monkeys: a non-human primate model for studying GnRH gene regulation. Mol Cell Endocrinol 117:121-130
72. Dong K W, Yu K L, Chen Z G, Chen Y D, Roberts J L 1997 Characterization of multiple promoters directing tissue-specific expression of the human gonadotropin-releasing hormone gene. Endocrinology 138:2754-2762
73. Chandran U R, Attardi B, Friedman R, Dong K W, Roberts J L, DeFranco D B 1994 Glucocorticoid receptor-mediated repression of gonadotropin-releasing hormone promoter activity in GT1 hypothalamic cell lines. Endocrinology 134:1467-1474
74. Dong K W, Chen Z G, Cheng K W, Yu K L 1996 Evidence for estrogen receptor-mediated regulation of human gonadotropin-releasing hormone promoter activity in human placental cells. Mol Cell Endocrinol 117:241-246
75. Joss J M, King J A, Millar R P 1994 Identification of the molecular forms of and steroid hormone response to gonadotropin-releasing hormone in the Australian lungfish, Neoceratodus forsteri. Gen Comp Endocrinol 96:392-400
76. Montero M, Le Belle N, King J A, Millar R P, Dufour S 1995 Differential regulation of the two forms of gonadotropin-releasing hormone (mGnRH and cGnRH-II) by sex steroids in the European female silver eel (Anguilla anguilla). Neuroendocrinology 61:525-535
77. Ikeda M, Taga M, Sakakibara H, Minaguchi H, Ginsburg E, Vonderhaar B K 1996 Gene expression of gonadotropin-releasing hormone in early pregnant rat and stesroid hormone exposed mouse uteri. J Endocrinol Invest 19:708-713
78. Gothilf Y, Meiri I, Elizur A, Zohar Y 1997 Preovulatory changes in the levels of three gonadotropin-releasing hormone-encoding messenger ribonucleic acids (mRNAs), gonadotropin B-subunit mRNAs plasma gonadotropin, and steroids in the female gilthead seabream, Sparus aurata. Biol Reprod 57:1145-1154
79. Bramley T A, McPhie C A, Menzies G S 1994 Human placental gonadotrophin-releasing hormone (GnRH) binding sites: III. Changes in GnRH binding levels with stage of gestation. Placenta 15:733-745
80. Lin L S, Roberts V J, Yen S S 1997 Expression of human gonadotropin-releasing hormone receptor gene in the placenta and its functional relationship to human chorionic gonadotropin secretion. J Clin Endocrinol Metab 80:580-585
81. Szilagyi A, Benz R, Rossmanith W G 1992 The human first-term placenta in vitro: regulation of hCG secretion by GnRH and its antagonist. Gynecol Endocrinol 6:293-300
82. Currie W D, Setoyama T, Lee P S, Baimbridge K G, Church J, Yuen B H, Leung P C 1993 Cytosolic free Ca2+ in human syncytiotrophoblast cells increased by gonadotropin-releasing hormone. Endocrinology 133:2220-2226
83. Emons G, Muller V, Ortmann O, Schulz K D 1998 Effects of LHRH-analogues on mitogenic signal transduction in cancer cells. J Steriod Biochem Mol Biol 65:1-6
84. Pahwa G S, Kullander S, Vollmer G, Oberheuser F, Knuppen R, Emons G 1991 Specific low affinity binding sites for goandotropin releasing hormone in human endometrial carcinoma. Eur J Obstet Gynecol Reprod Biol 41:135-142
85. Nagy A, Schally A V, Armatis P, Szepeshazi K, Halmos G, Kovacs M, Zarandi M, Groot K, Miyazaki M, Jungwirth A, Horvath J E 1996 Cytotoxic analogs of luteinizing hormone-releasing hormone containing doxorubicin or 2-pyrrolinodoxorubicin, a derivative 500-1000 times more potent. Proc Natl Acad Sci USA 93:7269-7273
86. Vincze B, Palyi I, Gaal D, Pato J, Mora M, Mezo I, Teplan I, Seprodi J 1996 In vivo studies of the new gonadotropin-releasing hormone antagonist-copolymer conjugates having antitumor activity. Cancer Detect Prey 20:153-159
87. Neri C, Berthois Y, Schatz B, Drieu K, Martin P M 1990 Compared effects of GnRH analogs and 4-hydroxytamoxifen on growth and steroid receptors in antiestrogen sensitive and resistant MCF-7 breast cancer cell sublines. Breast Cancer Res Treat 15:85-93
88. Crighton I L, Dowsett M, Lal A, Man A, Smith I E 1989 Use of luteinising hormone-releasing hormone agonist (Leuprorelin) in advanced post-menopausal breast cancer. Br J Cancer 60:644-648
89. Teodorczyk-Injeyan J, Jewett M A S, Kellen J A, Malkin A 1981 Gonadoliberin (LHRH) mediated release of choriogonadotropin in experimental human and animal tumors in vitro. Endocr Res Commun 8:19-24
90. Bruckner H W, Motwani B T 1989 Treatment of advanced refractory ovarian carcinoma with a gonadotropin-releasing hormone analogue. Clin Med 161:1216-1218
91. Cassano A, Astone A, Garufi C, Noviello M R, Pietrantonio F, Barone C 1987 A response in advanced post-menopausal breast cancer during treatment with the luteinising hormone releasing hormone agonist-Zoladex. Exp Biol Med 48:123-124
92. Klijn J G M, DeJong F H 1982 Treatment with a luteinising-hormone releasing-hormone analogue (Busereline) in premenopausal patients with metastatic breast cancer. Lancet 1982:1213-1216
93. Sealfon S C, Weinstein H, Millar R P 1997 Molecular mechanism of ligand interaction with the gonadotropin-releasing hormone receptor. Endocr Rev 18:180-205
94. Karten M J, Rivier J E 1986 Gonadotropin-releasing hormone analog design. Structure-function studies toward the development of agonists and antagonists: Rationale and perspective. Endocr Rev 7:44-66
95. Kang I S, Koong M K, Forman J S, Siler-Khodr T M 1991 Dose-related action of gonadotropin-releasing hormone on basal prostanoid production from the human term placenta. Am J Obstet Gynecol 165:1771-1776
96. Gautron J P, Pattou E, Kordon C 1981 Occurrence of higher molecular forms of LHRH in fractionated extracts from rat hypothalamus, cortex and placenta. Mol Cell Endocrinol 24:1-15
97. Mathialagan N, Rao A J 1986 Gonadotropin releasing hormone in first trimester human placenta: Isolation, partial characterisation and in vitro biosynthesis. J Biosci 10:429-441
98. Gautron J P, Pattou E, Bauer K, Rotten D, Kordon C 1989 LHRH-like immunoreactivity in the human placenta is not identical to LHRH. Placenta 10:19-35
99. Nowak R A, Wiseman B S, Bahr J M 1984 Identification of a gondotropin-releasing hormone-like factor in the rabbit fetal placenta. Biol Reprod 31:67-75(Abstr.)
100. Siler-Khodr, T. M. 1987. LHRH in pregnancy. In LHRH and Its Analogs: Contraceptive and Therapeutic Applications, Part II. B. H. Vickery and J. J. Nestor, Jr. editors. MTP Press, Ltd. Lancaster. 161-178.
101. Siler-Khodr, T. M. 1988. Hypothalamic-like activities of fetal membranes. In Proceedings of the 1st International Symposium on the Physiology of Human Fetal Membranes. J. Challis and B. Mitchell, editors. Perinatology Press, Ithaca, N.Y. 91-116.
102. Siler-Khodr T M, Kang I S, Jones M A, Harper M J K, Khodr G S, Rhode J 1989 Characterization and purification of a placental protein that inactivates GnRH, TRH and Angiotensin II. Placenta 10:283-296
103. Kang I S, Siler-Khodr T M 1992 Chorionic peptidase inactivates GnRH as a post-proline peptidase. Placenta 13:81-87
104. Kelsall R, Coe I R, Sherwood N M 1990 Phylogeny and ontogeny of gonadotropin-releasing hormone: Comparison of guinea pig, rat, and a protochordate. Gen Comp Endocrinol 479-494
105. Powell J F, Reska-Skinner S M, Prakash M O, Fischer W H, Park M, Rivier J E, Craig A G, Mackie G O, Sherwood N M 1996 Two new forms of gonadotropin-releasing hormone in a protochordate and the evolutionary implications. Proc Natl Acad Sci USA 93:10461-10464
106. Carolsfeld J, Powell J F F, Park M, Fischer W H, Craig A G, Chang J P, Rivier J E, Sherwood N M 2000 Primary structure and function of three gonadotropin-releasing hormones, including a novel form, from an ancient teleost, herring. Endocrinology 141:505-512
107. Powell J F, Zohar Y, Elizur A, Park M, Fischer W H, Craig A G, Rivier J E, Lovejoy D A, Sherwood N M 1994 Three forms of gonadotropin-releasing hormone characterized from brains of one species. Proc Natl Acad Sci USA 91:12081-12085
108. Montero M, Vidal B, King J A, Tramu G, Vandesande F, Dufour S, Kah O 1994 Immunocytochemical localization of mammalian GnRH (gonadotropin-releasing hormone) and chicken GnRH-II in the brain of the European silver eel (*Anguilla anguilla* L.). J Chem Neuroanat 7:227-241
109. White S A, Kasten T L, Bond C T, Adelman J P, Fernald R D 1995 Three gonadotropin-releasing hormone genes in one organism suggest novel roles for an ancient peptide. Proc Natl Acad Sci USA 92:8363-8367
110. Powell J F, Fischer W H, Park M, Craig A G, Rivier J E, White S A, Francis R C, Fernald R D, Licht P, Warby C, et al 1995 Primary structure of solitary form of gonadotropin-releasing hormone (GnRH) in cichlid pituitary; three forms of GnRH in brain of cichlid and pumpkinseed fish. Regul Pept 57:43-53
111. Zohar Y, Elizur A, Sherwood N M, Powell J F, Rivier J E, Zmora N 1995 Gonadotropin-releasing activities of the three native forms of gonadotropin-releasing hormone present in the brain of gilthead seabream, Sparus aurata. Gen Comp Endocrinol 97:289-299
112. Lin X W, Peter R E 1996 Expression of salmon gonadotropin-releasing hormone (GnRH) and chicken GnRH-II precursor messenger ribonucleic acids in the brain and ovary of goldfish. Gen Comp Endocrinol 101:282-296
113. Di Fiore M M, King J A, D'Aniello B, Rastogi R K 1996 Immunoreactive mammalian and chicken-II GnRHs in Rana esculenta brain during development. Regul Pept 62:119-124
114. Powell J F, Krueckl S L, Collins P M, Sherwood N M 1996 Molecular forms of GnRH in three model fishes: rockfish, medaka and zebrafish. J Endocrinol 150:17-23
115. Iela L, Powell H E, Sherwood N M, D'Aniello B, Rastogi R K, Bagnara J T 1996 Reproduction in the Mexican leaf frog, Pachymedusa dacnicolor. VI. Presence and distribution of multiple GnRH forms in the brain. Gen Comp Endocrinol 103:235-243
116. Powell J F, Standen E M, Carolsfeld J, Borella M I, Gazola R, Fischer W H, Park M, Craig A G, Warby C M, Rivier J E, Val-Sella M V, Sherwood N M 1997 Primary structure of three forms of gonadotropin-releasing hormone (GnRH) from the pacu brain. Regul Pept 68:189-195
117. Dellovade T L, King J A, Millar R P, Rissman E F 1993 Presence and differential distribution of distinct forms of immunoreactive gonadotropin-releasing hormone in the musk shrew brain. Neuroendocrinology 58:166-177
118. King J A, Steneveld A A, Curlewis J D, Rissman E F, Millar R P 1994 Identification of chicken GnRH II in brains of metatherian and early-evolved eutherian species of mammals. Regul Pept 54:467-477
119. Kasten T L, White S A, Norton T T, Bond C T, Adelman J P, Fernald R D 1996 Characterization of two new pre-proGnRH mRNAs in the tree shrew: first direct evidence for mesencephalic GnRH gene expression in a placental mammal. Gen Comp Endocrinol 104:7-19
120. Jimenez-Linan M, Rubin B S, King J C 1997 Examination of guinea pig luteinizing hormone-releasing hormone gene reveals a unique decapeptide and existence of two transcripts in the brain. Endocrinology 138:4123-4130
121. White S A, Bond C T, Francis R C, Kasten T L, Fernald R D, Adelman J P 1994 A second gene for gonadotropin-releasing hormone: cDNA and expression pattern in the brain. Proc Natl Acad Sci USA 91:1423-1427
122. Lin X W, Peter RE 1997 Cloning and expression pattern of a second [His5Trp7Tyr8]gonadotropin-releasing hormone (chicken GnRH-H-II) mRNA in goldfish: evidence for two distinct genes. Gen Comp Endocrinol 107:262-272
123. Siler-Khodr T M, Grayson M 1999 Comparison of GnRH and its synthetic and naturally occurring analogs for binding to the human placental receptor. J Soc Gynecol Invest 6:225 A(Abstr.)
124. Siler-Khodr T M, Grayson M 2000 Inhibiton of human trophoblast function by superagonists of chicken II GnRH. J Soc Gynecol Invest 7:280 A(Abstr.)
125. Mezo I, Seprodi J, Vincze B, Palyi I, Keri G, Vadasz Z, Toth G, Kovacs M, Koppan M, Horvath J E, Kalnay A, Teplan I 1996 Synthesis of GnRH analogs having direct antitumor and low LH-releasing activity. Biomedical Peptides, Proteins & Nucleic Acids 2:33-40
126. Mezo I, Lovas S, Palyi I, Vincze B, Kalnay A, Turi G, Vadasz Z, Seprodi J, Idei M, Toth G, Gulyas E, Otvos F, Mak M, Horvath J E, Teplan I, Murphy RF 1997 Synthesis of gonadotropin-releasing hormone III analogs. Structure-antitumor activity relationships. J Med Chem 40:3353-3358

We claim:

1. A Chicken II GnRH analog, having the sequence as defined in SEQ ID NO:7 (p-Glu-His-Trp-Ser-His-Xaa[1]-Trp-Tyr-Pro-Xaa[2]), wherein said analog is capable of binding to tumor cell GnRH receptors with greater affinity than mammalian GnRH and is active in the presence of a post-proline peptidase or endopeptidase, wherein said Chicken II GnRH analog has a D-amino acid substitution at position 6 and a post-proline peptidase inhibitor at position 10, said post-proline peptidase inhibitor being aza-Gly-amide.

2. The Chicken II GnRH analog of claim 1 wherein said Chicken II GnRH analog is further defined as an anti-tumor agent.

3. The Chicken II GnRH analog of claim 1 wherein said Chicken II GnRH analog is further defined as an anti-proliferative agent.

4. The Chicken II GnRH analog of claim 3 wherein said Chicken II GnRH analog is further defined as an anti-metastatic agent.

5. The Chicken II GnRH analog of claim 4 wherein said Chicken II GnRH analog is further defined as an apoptotic agent.

6. The Chicken II GnRH analog of claim 1 wherein said Chicken II GnRH analog is D-Arg(6)-Chicken II GnRH-aza-Gly(10)-amide.

7. The Chicken II GnRH analog of claim 1 wherein said D-amino acid substituted at position 6 is selected from the group consisting of D-Arg, D-Leu, D-tBu-Ser, and D-Trp.

* * * * *